United States Patent [19]

Raniere et al.

[11] Patent Number: 4,724,272
[45] Date of Patent: Feb. 9, 1988

[54] METHOD OF CONTROLLING PYROLYSIS TEMPERATURE

[75] Inventors: Frederick D. Raniere, Northridge; Merlin D. Schuman, Canoga Park, both of Calif.

[73] Assignee: Rockwell International Corporation, El Segundo, Calif.

[21] Appl. No.: 601,242

[22] Filed: Apr. 17, 1984

[51] Int. Cl.$^4$ .............................................. C07C 2/00
[52] U.S. Cl. .................................. 585/500; 585/539; 585/540; 585/652; 585/943; 208/129; 208/130
[58] Field of Search ............... 585/539, 540, 652, 648, 585/500, 943; 208/129, 130

[56] References Cited

U.S. PATENT DOCUMENTS

| | | | |
|---|---|---|---|
| 2,767,233 | 10/1956 | Mullen et al. | 260/679 |
| 2,790,838 | 4/1957 | Schrader | 260/679 |
| 2,908,733 | 10/1959 | Sage | 585/540 |
| 2,912,475 | 11/1959 | Krause et al. | 260/679 |
| 2,985,698 | 5/1961 | Pechtold et al. | 585/650 |
| 3,047,371 | 7/1962 | Krause et al. | 585/539 |
| 3,408,417 | 10/1968 | Sogawa et al. | 260/679 |
| 3,419,632 | 12/1968 | Sogawa et al. | 585/539 |
| 3,563,709 | 2/1971 | Staud | 23/277 |
| 3,692,862 | 9/1972 | Staud et al. | 585/539 |
| 4,136,015 | 1/1979 | Kamm et al. | 585/648 |

FOREIGN PATENT DOCUMENTS

| | | | |
|---|---|---|---|
| 680773 | 2/1964 | Canada | 585/539 |
| 823376 | 4/1981 | U.S.S.R. | 585/539 |

Primary Examiner—Curtis R. Davis
Assistant Examiner—Chung K. Pak
Attorney, Agent, or Firm—H. Fredrick Hamann; Harry B. Field; Clark E. DeLarvin

[57] ABSTRACT

A method of controlling temperature during a pyrolysis reaction wherein the predominant pyrolysis reactions are endothermic. A fuel and oxidizer are combusted in a combustion zone to produce a hot gas stream at a superatmospheric pressure. The hot gas stream is then passed through a converging-diverging nozzle to accelerate the hot gas stream to a velocity of at least about mach 2. The reactant to be pyrolyzed is injected into the supersonic hot gas stream to produce a reaction mixture flowing at supersonic velocity and initiate the endothermic pyrolysis reactions. Substantially immediately thereafter the velocity of the reaction mixture is reduced over a predetermined reaction time to convert the kinetic energy of the reaction mixture to thermal energy in an amount sufficient to substantially offset the endothermic reactions taking place while maintaining supersonic flow. At the end of the predetermined reaction time the velocity of the reaction mixture is reduced to subsonic flow and the reaction quenched. The present invention is particularly adapted to the pyrolysis of methane to produce acetylene and ethylene by contacting the methane with hot gases resulting from the reaction of hydrogen with oxygen.

10 Claims, 2 Drawing Figures

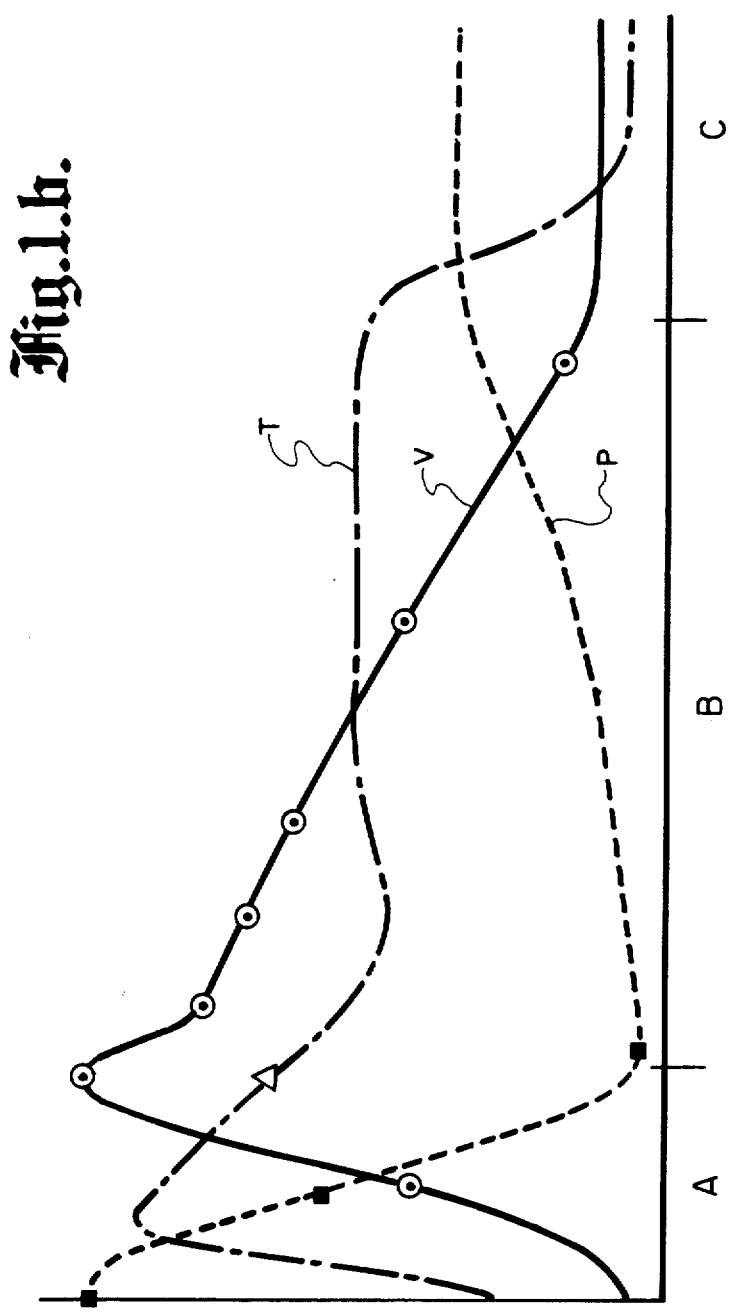
Fig.1.b.

METHOD OF CONTROLLING PYROLYSIS TEMPERATURE

The present invention broadly relates to the thermal conversion of hydrocarbons and the control of temperature during such conversion to produce enhanced yields of more valuable products. It particularly relates to the control of temperature during such a process which involves rapid heating, mixing and short residence times to produce enhanced yields of, for example, acetylene and olefins.

It is well known that hydrocarbons may be converted to more valuable products, such as olefins, by thermal cracking (pyrolysis). In many of the prior art processes, steam is used as the heat transfer fluid to convert gaseous hydrocarbon feed stocks to olefins.

U.S. Pat. No. 2,912,475 relates to the manufacture of low molecular weight unsaturated hydrocarbons (olefins). The patent discloses a process wherein extremely hot combustion gases are mixed with a secondary lower temperature gas stream containing steam or hydrogen, and which is free of any molecular oxygen. Thereafter the combined stream is passed through a restricted opening into a reaction zone wherein the stream is contacted with a hydrocarbon to pyrolyze the hydrocarbon and form the desired olefin product.

U.S. Pat. No. 2,767,233 describes a method of effecting thermal transformation of hydrocarbons. The method comprises continuously burning a flowing mixture of fuel and gaseous oxidant within an elongated chamber and exhausting the resulting gases at static pressure of not more than about one-half of the pressure of combustion and producing within the chamber a high-temperature zone in at least a part of which the gaseous combustion products flow at a velocity of at least 1000 feet/second. The rate of supply of said mixture and the mixture of fuel and oxidant is such as to produce within the high temperature zone a temperature of at least 1400° K. An aliphatic hydrocarbon is introduced into the high temperature zone and the reaction products resulting therefrom quickly cooled and recovered. The patent teaches that the method is particularly effective for the production of acetylene.

U.S. Pat. No. 2,908,733 describes a partial oxidation process wherein a gas form reactant is converted to a gas form reaction product and wherein the reaction product yield is favorably effected by elevated temperature. In accordance with patentee's teaching, a gas form reactant is introduced as a continuous stream into a primary reaction zone at a velocity of about 1000 feet/second. Thermal energy is imparted to the gas form reactant in the primary reaction zone by exothermic reaction of the reactant to raise the reactant to an elevated temperature while maintaining velocity above about 1000 feet/second to effect conversion of at least a portion of the reactant to a gas form reaction product. Thereafter, the resulting stream is decelerated along a path of flow of continually increasing cross-section area into a second reaction zone of a greater cross-sectional area than the first reaction zone, such that the kinetic energy of the stream is converted to thermal energy to increase the temperature and pressure of the stream to a temperature and pressure in excess of that in the first reaction zone and produce an increased yield of the reaction product.

U.S. Pat. Nos. 2,790,838 and 3,408,417 describe processes which involve the thermal cracking or pyrolysis of hydrocarbons. These patents discuss the advantages of a venturi constriction or nozzle to enhance mixing.

U.S. Pat. No. 3,563,709 addresses the same problem to which applicants' invention is directed; namely, that of maintaining temperature during an endothermic cracking process. In accordance with the process disclosed therein a hydrocarbon is pyrolyzed to lower unsaturated aliphatic hydrocarbons by mixing the hydrocarbon with hot combustion gases at a rate sufficient to heat the mixture above the pyrolyzing temperature. The endothermic reaction takes place in a tube having a porous wall. Oxygen is forced into the tube through the porous wall to supply the thermal energy consumed and to maintain the pyrolysis temperature by oxidation of a portion of the pyrolysis product. Thus, this is another partial oxidation process.

A basic problem with partial oxidation processes is that they must utilize extensive quantities of oxygen to initiate and sustain adequate conversion of, for example, methane. In such processes there typically will be formed high concentration of radicals such as OH, and O which will in turn produce large byproduct yields of carbon oxides, principally CO. Obviously, the formation of large byproduct yields of carbon oxides has a deleterious effect on the yield of the desired products or intermediate products such as, for example, acetylene or ethylene.

Other processes have been suggested for thermal cracking of hydrocarbons to produce more valuable products which use chlorine as an oxidizer or an electric arc for thermal cracking. It is not believed, however, that any of these processes have achieved any significant degree of commercial acceptance.

SUMMARY OF INVENTION

The present invention provides a method of controlling temperature during a pyrolysis reaction wherein the predominant pyrolysis reactions are endothermic. Thus, the present invention is particularly applicable to the thermal cracking of hydrocarbons wherein the hydrocarbons are rapidly heated and quenched to obtain certain desired intermediate reaction products such as acetylene and olefins.

In accordance with the present invention a fuel and oxidizer are introduced into a combustion zone and combusted to produce a hot gas stream at a superatmospheric pressure. The hot gas stream is then passed through a converging-diverging nozzle to accelerate the hot gas stream to a velocity of at least about mach 2. This acceleration results in a reduction in both pressure and temperature. The reactant to be pyrolyzed is injected into the hot gas stream to produce a reaction mixture flowing at supersonic velocity and initiate the endothermic pyrolysis reactions. Substantially immediately thereafter the velocity of the reaction mixture is reduced over a predetermined reaction time to convert the kinetic energy of the reaction mixture to thermal energy in an amount sufficient to substantially offset the effects of the endothermic reactions taking place to produce the desired intermediate reaction products while maintaining supersonic flow. This balance between the thermal energy generated by reducing the velocity of the reaction mixture and the thermal energy consumed by the endothermic reactions taking place makes it possible to maintain the temperature in a range which favors formation of the desired intermediate reaction products. At the end of the predetermined reaction time, the velocity of the reaction mixture is reduced to subsonic flow and the reaction quenched to prevent the desired intermediate reaction products from further reacting to form less desirable equilibrium reaction products.

The advantages of the present invention are accomplished in four stages. In the first stage, the hot gas for the pyrolysis reaction is produced by reacting a fuel with an oxidizer to produce a hot gas stream at an elevated temperature and pressure. The fuel utilized may be any combustible material which will react with the oxidizer to produce a substantially gaseous stream free of erosive solids. Such fuels would include the various petroleum and petroleum byproducts such as residue, methane, hydrogen, and the like. However, in accordance with a particularly preferred embodiment of the invention, the fuel is hydrogen for reasons which will be discussed later. The hydrogen may be introduced alone or in combination with another fuel such as methane and also may include superheated steam.

In a similar manner, the oxidizer to be used may be any gaseous or liquid compound which will react with the fuel to form hot gaseous combustion products. Air is a readily available and inexpensive oxidizer and its use is suited for the practice of the present invention. There is required only sufficient pumping capacity to provide the necessary quantities of air at the pressures desired in the combustion chamber. A disadvantage of using air, however, resides in the large quantity of nitrogen present which acts only as a diluent requiring the expenditure of thermal energy to heat, and further complicates subsequent separation steps after the desired reactions have taken place. Thus, the particularly preferred oxidizer is relatively pure oxygen. This is particularly true when utilizing the preferred fuel hydrogen, since the combustion product is water which is readily separable from the pyrolysis reaction products. In all instances, however, it is preferred that the oxidizer be present in an amount less than that stoichiometrically required to react with all the fuel. The purpose for this fuel-rich combustion is to avoid the possibility of the presence of any unreacted oxygen which could react with the reactant to form undesirable byproducts such as carbon oxides. The temperature of the combustion products and pressure are not particularly critical provided, however, that they must be at a higher temperature and pressure than that desired for the subsequent pyrolysis reaction.

In the next stage, the hot gases of combustion are passed through a converging-diverging nozzle to accelerate them to a velocity at least in excess of mach 1.5 and preferably at least mach 2. A key feature of this stage is that the pressure and temperature in the combustion zone are selected such that, after the hot gases have been accelerated to a desired supersonic velocity which will result in a decrease in temperature and pressure, the decreased temperature and pressure are those which favor production of the desired intermediate reaction products and which will minimize formation of any undesirable byproducts.

In the third stage, the reactant is added to the supersonic flow of hot combustion gases. A key feature of this stage is that the reactant mixture is maintained at a temperature which favors production of the desired intermediate products by reducing the velocity of the hot gas stream to convert its kinetic energy to thermal energy in an amount sufficient to offset the temperature reducing endothermic pyrolysis reactions which are taking place. In addition, during this velocity reduction, the initial velocity is selected such that substantially throughout a predetermined reaction time the mixture is maintained above sonic velocity. Supersonic velocity is required in order to utilize a reactor having an adequate length to ensure uniform mixing while maintaining the very short residence time required to prevent the desired intermediate reaction products from further reacting to form less desirable products.

The fourth stage comprises a rapid reduction in the temperature of the reaction mixture to arrest the reactions and prevent the desired intermediate reaction products from further reacting to form those products which would result if the reaction were allowed to proceed to equilibrium. The reaction is quenched by rapidly reducing the velocity of the gas reaction mixture by introducing it into an area of expanding cross-sectional flow area and by contacting the reaction mixture in direct or indirect heat exchange relationship with a cooling fluid or both. Preferably the reaction mixture is introduced into an area of expanded cross-sectional flow area and concurrently contacted directly with a cooling medium.

The fuel, reactant, temperatures, pressure and the like will be for the most part a matter of design choice depending upon the particular products desired. Such selection, however, is believed to be well within the skill of those versed in the art.

BRIEF DESCRIPTION OF THE DRAWINGS

The method of the present invention will now be more fully described with specific reference to a particularly preferred embodiment and the appended drawings in which:

FIG. 1.$b$ is a graph of pressure (P), temperature (T), and velocity (V) as a function of reactor length related to the apparatus depicted in FIG. 1.$a$.

DESCRIPTION OF A PREFERRED EMBODIMENT

Figure 1A:
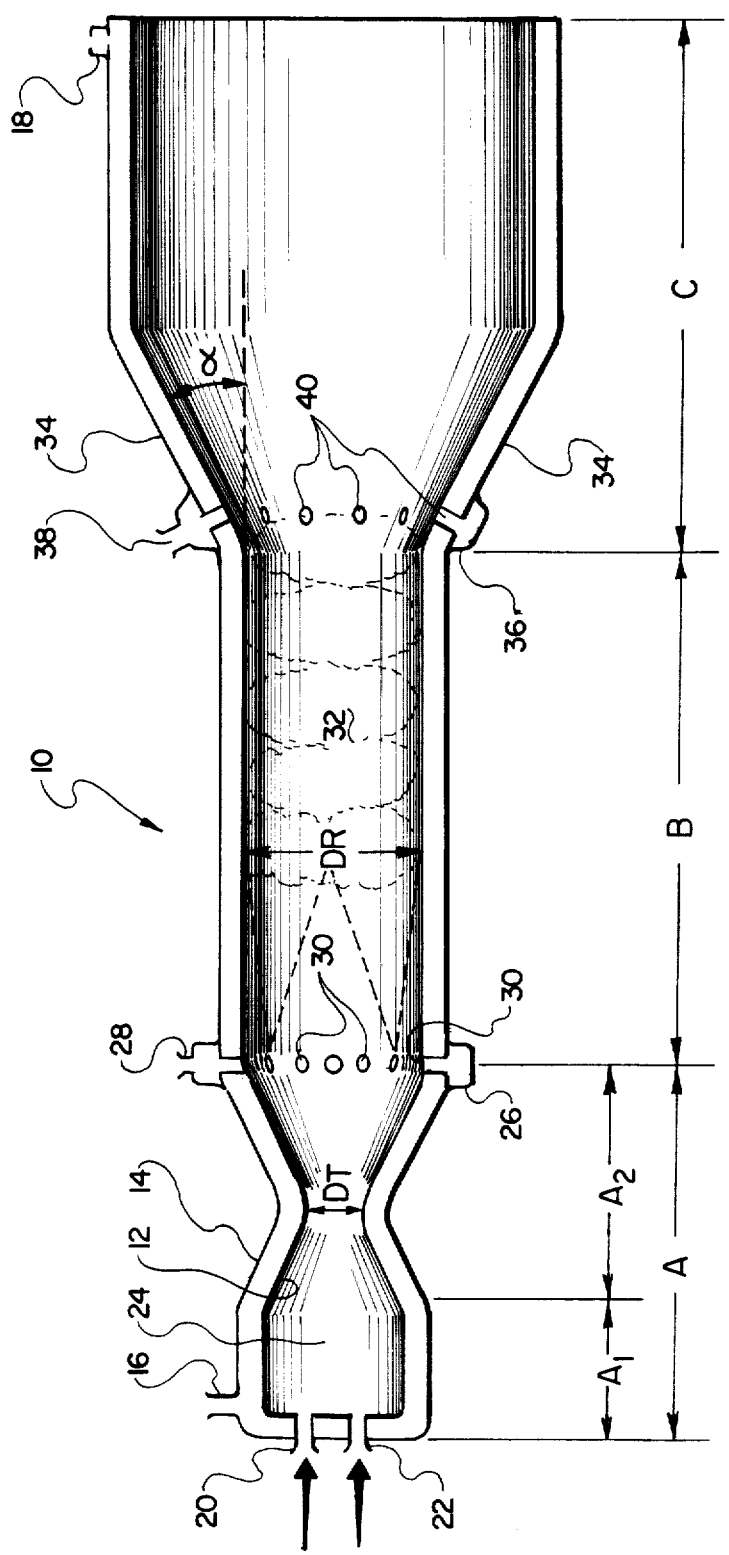
FIG. 1.$a$ is a schematic sectional view of a reactor for practicing the present method for temperature control during pyrolysis of a hydrocarbon.

Referring specifically to FIGS. 1.$a$ and 1.$b$, the present invention will now be described with respect to a particularly preferred embodiment of the invention; namely, one in which hydrogen and oxygen are combusted to produce a hot gas stream for the pyrolysis of methane to produce at least one member selected from the group consisting of ethylene and acetylene. In FIG. 1.$a$, there is depicted a reactor 10 for practicing the method of the present invention. Reactor 10 comprises an inner wall 12 and an outer wall 14 having a passageway therebetween for a coolant fluid. The coolant fluid flows through a coolant inlet 16 through the passageway and leaves through a coolant outlet 18. It will be appreciated that the direction of flow of the coolant fluid could be altered. In addition, multiple inlets and outlets could be provided such that the coolant fluid does not flow the full length of reactor 10. In accordance with the preferred embodiment the coolant fluid is water such that the thermal energy is recoverable as steam from the coolant outlet.

Hydrogen and oxygen are introduced through fuel and oxygen inlets 20 and 22, respectively. The oxygen is introduced in an amount less than that required to react with all of the hydrogen. Generally, the oxygen will be introduced in an amount of from about 60 to 95% of that stoichiometrically required to react with all of the hydrogen. The hydrogen and oxygen are reacted and combusted in a combustion zone 24 within reactor 10 to produce a hot gas stream typically having a temperature of from about 2000° to 3000° C. and a pressure of about three atmospheres or higher. Combustion zone 24 will have a length $A_1$ which is sufficient to insure that the reaction between the hydrogen and oxygen is substantially complete. The hot gas stream from combustion zone 24 is passed through a converging-diverging nozzle extending over a length $A_2$ of reactor 10, through which the hot gas is accelerated to a velocity of at least about mach 2 and preferably in excess of about mach 2.5. The nozzle has a minimum cross-sectional flow area at its throat DT and diverges in a downstream direction to a maximum cross-sectional flow area DR. The ratio of DR to DT, referred to herein as the expansion ratio, is selected to ensure the desired supersonic flow. Generally, the expansion ratio will be at least about 7:1 and typically will be about 8:1 or higher.

Reactor 10 further includes a manifold 26 provided with an inlet 28 for the introduction of the reactant to be thermally cracked (pyrolyzed) which, as depicted, enters through a plurality of injection ports 30 where it contacts the hot gas stream in reaction zone 32. Reaction zone 32 has a length B sufficient to provide a desired reaction time. Reaction zone 32 ends in a terminal or downstream section which is provided with a diverging wall 34 to provide an increased cross-sectional flow area and produce a reduction in the velocity of the gases flowing therethrough. Walls 34 diverge at an angle $\alpha$ of less than 10° and preferably an angle of about 6°. Advantageously there also is provided adjacent the terminal or downstream section of reaction zone 32 a manifold 36 provided with an inlet 38 for the introduction of a cooling medium through a plurality of injection ports 40. This downstream section of reactor 10 including diverging wall 34 and cooling manifold 36, comprise a quench zone C of reactor 10.

In operation, hydrogen and substantially pure oxygen are introduced into combustion zone 24 in an amount to produce a hot gas stream having a temperature in the range of from about 2000° to 3500° C., preferably 2000° to 3000° C., at a pressure of about three atmospheres. The hot gas stream flows through the converging-diverging nozzle and is contacted with streams of methane introduced through injection ports 30. After passing through the converging-diverging nozzle, the hot gas stream has a temperature of from about 1500° to 2000° C. and is at a pressure less than atmospheric, generally less than about 0.5 atmosphere and preferably from about 0.03 to 0.2 atmosphere. The hot gas stream and methane mix to produce a high velocity (supersonic) flowing reaction mixture. The velocity of the reaction mixture is reduced over the length B of reaction zone 32 to convert the kinetic energy of the reaction mixture to thermal energy in an amount to offset the endothermic reactions taking place, such that the temperature throughout the length of reacton zone B is maintained within the range of from about 1500° to 2000° C., which temperature favors the formation of ethylene and acetylene and minimizes the formation of any undesirable side or byproducts. The velocity of the mixture in reaction zone 32 and the length B of reactor 10 are selected to provide a reaction time of less than about 1 msec and preferably about ½ msec to obtain enhanced yield of the desired products.

It is a key feature of the present invention that throughout substantially the entire length B of reactor 10, the reaction mixture is maintained in excess of sonic velocity. Thus, throughout at least about 70% and preferably 90% of reaction zone 32, the reaction mixture flows at supersonic velocity. In addition, it is preferred that the initial velocity of the hot gas stream entering reaction zone 32 be such that by the time the reaction mixture reaches the downstream end of reaction zone 32, it is at or below sonic velocity to reduce energy losses.

At the end of reaction zone 32, the reaction mixture is rapidly quenched by reducing the velocity of the mixture to substantially less than sonic, preferably less than about mach 0.5. In accordance with a particularly preferred embodiment, the reaction mixture is concurrently directly or indirectly contacted with a coolant medium to quench the reaction by reducing the temperature of the reaction mixture to less than about 800° C. to prevent any of the desired intermediate reaction products formed from further reacting to produce less desirable equilibrium reaction products. The coolant medium may be a hydrocarbon, water, or an inert gas.

The reaction mixture leaving the quench portion C of reactor 10 is recovered and processed for recovery of the acetylene and ethylene. In addition, any unreacted methane is recovered for recycle to the process, utilizing known gas separation techniques. Further, any remaining hydrogen or hydrogen produced in reaction zone 32 is separately recovered and recycled to combustion zone 24.

In accordance with the present invention, it has been found that as much as 60% or more of the methane may be converted to desired intermediate reaction products, i.e., ethylene and acetylene, in a single pass through reactor 10.

EXAMPLE

To further demonstrate the present invention, an apparatus substantially the same as that described and shown in the drawing is utilized and operated in accordance with the foregoing parameters. The reactor is designed to process 1500 tons/day of methane. The reaction mixture after quench is recovered, subjected to cryogenic separation and produces 1171 tons/day of acetylene and 43 tons/day of ethylene. In addition, there is recovered 474 tons/day of methane for recycle to the process and 493 tons/day of hydrogen for recycle to combustion zone 24. It is a particular advantage of the present invention that only 6 tons/day of the feed are converted to solid carbon or soot and 138 tons/day to undesired carbon oxide byproducts. Thus, it is seen that in excess of 60% of the initial methane feed is converted to desired olefin intermediate products. By way of contrast, under substantially the same conditions but without maintaining supersonic flow and heat generation in reaction zone 32, less than about 30% of the methane feed is converted to the desired acetylene and olefin intermediate products.

While the present invention has been described in terms of a specific example, and what is now considered its best mode of practice, it will be appreciated by those skilled in the art that various changes and modifications are possible which will not depart from the spirit or scope of the inventive concepts taught herein. Thus, the invention has been described with respect to certain presently preferred specific operating parameters and reactants. However, it is within the scope of the present invention to utilize other parameters and other reactants. Thus, the foregoing description and example are intended to be illustrative only and should not be construed as limiting the scope of the invention, reference being made to the appended claims for this latter purpose.

What is claimed is:

1. A method of controlling temperature during pyrolysis of methane wherein the predominant reactions are endothermic and the reaction is rapidly quenched to obtain at least one intermediate reaction product selected from the group consisting of acetylene and ethylene comprising the sequential steps of:

(a) introducing hydrogen and substantially pure oxygen into a combustion zone, said hydrogen being present in an amount in excess of that required to react with all of the oxygen, and combusting them to produce a hot gas stream comprising steam and a minor amount of unreacted hydrogen, having a temperature of from 2000°–3500° C. and a pressure of at least three atmospheres;

(b) passing the hot gas stream through a converging-diverging nozzle, said nozzle having an expansion ratio sufficient to accelerate the hot gas stream to a velocity of at least mach 2.0 along with a corresponding reduction in pressure and temperature, the reduced temperature being in the range of 1500°–2000° C. and the reduced pressure being subatmospheric;

(c) injecting the methane to be pyrolyzed into the hot gas stream to produce a reaction mixture flowing at supersonic velocity and initiate the endothermic pyrolysis reactions;

(d) reducing the velocity of the reaction mixture over a predetermined reaction time to convert the kinetic energy of the reaction mixture to thermal energy in an amount sufficient to substantially offset the effects of the endothermic reactions taking place to convert at least about 60% of the methane to the selected intermediate products and produce enhanced yields of the selected intermediate reaction produce while maintaining supersonic flow;

(e) reducing the velocity of the reaction mixture to subsonic flow and concurrently quenching the reaction; and recovering the selected intermediate reaction products.

2. The method of claim 1 wherein in step (b) the hot gas stream has a velocity of about mach 2.5.

3. The method of claim 2 wherein in step (b) the pressure is in the range of from about 0.03 to 0.2 atmosphere.

4. The method of claim 3 wherein in step (d) said reaction time is less than about 2 msec.

5. The method of claim 4 wherein in step (d) said predetermined reaction time is about 0.5 msec and said desired intermediate reaction product is acetylene.

6. The method of claim 4 wherein in step (e) the velocity is reduced to less than about mach 0.5.

7. The method of claim 6 wherein in step (e) the velocity is reduced by introducing the reaction mixture into an area of increased cross-sectional flow area.

8. The method of claim 6 wherein in step (e) the reaction mixture is quenched by direct contact with a cooling fluid.

9. The method of claim 8 wherein the cooling fluid is a hydrocarbon.

10. The method of claim 8 wherein in step (e) the cooling fluid is water.

* * * * *

UNITED STATES PATENT AND TRADEMARK OFFICE
CERTIFICATE OF CORRECTION

PATENT NO. : 4,724,272

DATED : Feb. 9, 1988

INVENTOR(S) : Frederick D. Raniere and Merlin D. Schuman

It is certified that error appears in the above-identified patent and that said Letters Patent are hereby corrected as shown below:

Claim 1, Col. 8, line 6 change "produce" to read --product--.

Signed and Sealed this

Fifth Day of July, 1988

Attest:

DONALD J. QUIGG

Attesting Officer

Commissioner of Patents and Trademarks